US00PP16193P2

(12) United States Plant Patent
Olesen et al.

(10) Patent No.: US PP16,193 P2
(45) Date of Patent: Jan. 10, 2006

(54) ***CLEMATIS* PLANT NAMED 'EVIPO032'**

(50) Latin Name: *Clematis viticella*
Varietal Denomination: Evipo032

(75) Inventors: Mogens N. Olesen, Fredensborg (DK); Raymond J. Evison, St. Sampsons (GB)

(73) Assignee: Poulsen Roser A/S, Fredensborg (DK)

( * ) Notice: Subject to any disclaimer, the term of this patent is extended or adjusted under 35 U.S.C. 154(b) by 121 days.

(21) Appl. No.: 10/897,919

(22) Filed: Jul. 23, 2004

(51) Int. Cl.
*A01H 5/00* (2006.01)

(52) U.S. Cl. ..... Plt./228
(58) Field of Classification Search ..... Plt./228
See application file for complete search history.

*Primary Examiner*—Kent Bell

(57) ABSTRACT

A new *Clematis* cultivar which is well suited to propagation in glasshouses. With a tall growth habit, profuse, deep violet flowers and continuous summer flowering. The variety successfully propagates from softwood cuttings and is suitable for cultivation in commercial glasshouses. This new and distinct variety has shown to be uniform and stable in the resulting generations from asexual propagation.

3 Drawing Sheets

Botanical classification: *Clematis l. Genus—Clematis.* Species—*viticella.*
Variety denomination: 'Evipo032'.

SUMMARY OF THE DISCOVERY

The present invention constitutes a new and distinct variety of *Clematis* which originated as a chance seedling of unknown parents. The new variety is named 'Evipo032'.

The objective of the selection of this *Clematis* variety for commercial glasshouse and nursery culture was to create a new and distinct variety with unique qualities that this variety has:

1. Profuse deep violet flowers;
2. Reliable and repeatable production plant;
3. Summer flowering;
4. Improved disease resistance.

These qualities required improvement in *Clematis* varieties that were in commercial cultivation and the objectives have been substantially achieved in the new variety, as evidenced by the unique combination of characteristics that are present in 'Evipo032', which distinguish it from all other varieties of which we are aware.

Evaluations of the seedling plant were conducted in a controlled environment. As a result, 'Evipo032' was selected by Raymond J. Evison and Mogens N. Olesen in their *Clematis* development program in Domarie Vineries Les Sauvagees, St. Sampsons, Guernsey, Channel Islands, United Kingdom in June 1996.

Asexual reproduction of 'Evipo032' by cuttings was first done by Raymond J. Evison and Mogens N. Olesen in Domarie Vineries Les Sauvagees, St. Sampsons, Guernsey, Channel Islands, United Kindgom in April 1997. This initial and subsequent asexual propagations have demonstrated that the characteristics of 'Evipo032' are true to type and are transmitted from one generation to the next.

BRIEF DESCRIPTION OF THE DRAWING

The accompanying color illustrations show as true as is reasonably possible to obtain in color photographs of this type:

FIG. 2.2 Stem showing branching and the attachment of leaves and flower buds;

FIG. 2.3 Flower bud closed and ¼ open;

FIG. 2.4 Stem showing attachment of mature and juvenile leaves.

DETAILED DESCRIPTION OF THE VARIETY

Figure 1:
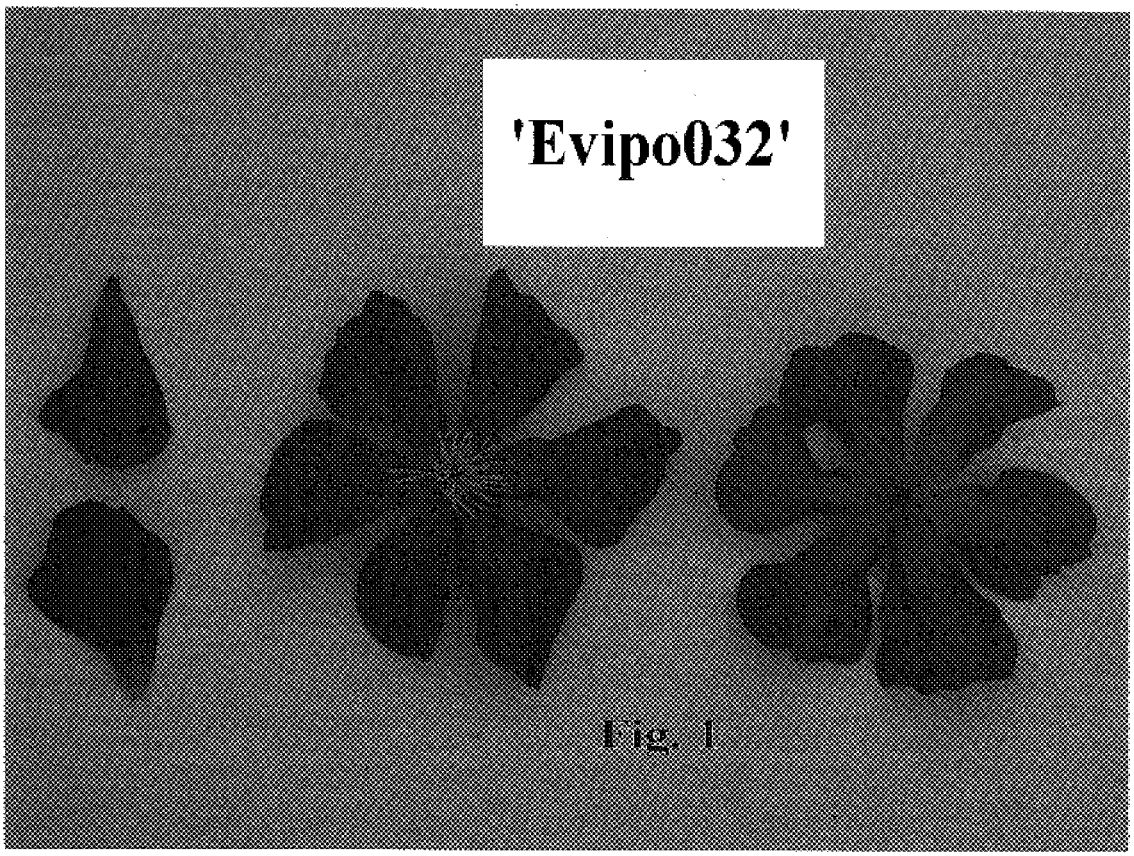
FIG. 1 Enlarged image of open flower, upper and lower surface and tepals detached.

The following is a detailed description of 'Evipo032', as observed in its growth throughout the flowering period in glasshouses at Domarie Vineries Les Sauvagees, St. Sampsons, Guernsey, Channel Islands, United Kingdom. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001.

For a comparison, the nearest existing *Clematis* variety is 'Blue Belle', a non-patented variety. Chart 1 details several physical characteristics of 'Evipo032' and the comparison variety.

CHART 1

| | 'EVIPO032' | 'BLUE BELLE' |
|---|---|---|
| Tepal Count | Normally 6 | 4 to 6 |
| Tepal arrangement | Very regular | Variable, irregular arrangement |
| Flower center/reproductive organs | Below average quantity of stamens. Stamens are also held fairly tightly. | More significant flower center a greater quantity of stamens and wider opening of stamens. |

FLOWER AND FLOWER BUD

Blooming habit: Summer flowering. Normal flowering months are May, June, July, August, September.

Flower bud:

*Size.*—12 to 15 mm in length. Bud diameter is 7 mm.

*Bud form.*—Ovate to elliptical.

*Bud color.*—Purple Group N79B.

Peduncle:

*Aspects.*—Near vertical.

*Surface.*—Smooth and pubescent.

*Length.*—145 to 160 mm average length.

*Color.*—Greyed-Purple Group N187B.

*Strength.*—Moderately strong.

Receptacle: Absent.

Flower arrangement:

*Location on vine.*—Flowering normally occurs on new growth.

*Borne.*—Compound cyme cluster of 3 to 5 flowers.

Flower bloom:

*Size.*—92 to 97 mm in diameter. 20 mm in depth.

*Profile.*—Upon opening: Flowers are flat. After opening: Flowers are flat with tepals reflexing somewhat.

*Tepal color.*—Upon opening: Upper surface is Violet Group 86A in color. After opening: Upper surface is Violet Group 86B in color. Lower surface is Violet Group 86B.

*Variations.*—Violet Group 85C at tepal base.

*Fragrance.*—None.

*Lasting quality on plant.*—10 to 15 days.

*Lasting quality as a cut flower.*—4 to 5 days.

Tepals:

*Quantity.*—Normally 6 tepals. However, occasionally 4 or 5 tepals have been observed.

*Size.*—42 to 50 mm in length by 28 to 30 mm wide.

*Shape.*—Individual tepal shape is obovate.

*Undulation of margin.*—Weak and weakly serrated.

*Tepal apex.*—Cuspidate.

*Recurvature of tip.*—Reflexed somewhat.

*Persistence.*—Tepals drop off cleanly.

*Arrangement.*—Tepals are arranged regularly.

Reproductive organs:

*Arrangement.*—Open.

*Pollen.*—Quantity: Below average. Color: Yellow Group 12D.

*Anthers.*—Size: 5 mm in length. Color: Yellow Group 12D. Quantity: 45 to 60.

*Filaments.*—Color: White Group N155A. Violet Group 85C observed at filament base. Length: 7 mm.

*Pistils.*—Quantity: 35 to 42.

*Stigmas.*—Inferior to anthers, becoming superior as the flower opens.

*Styles.*—Color: White Group 155B with base covered with feathery sheath of Greyed-Yellow Group 162B. Length: 12 to 14 mm.

Seed head characteristics:

*Size.*—Approximately 55 mm in diameter at the base.

*Shape.*—Tear shaped with approximately 8 mm diameter with elongated plumule. Length of plumule 30 mm.

PLANT

Plant form: Climbing.

Size: Seasons growth attains 2 to 2.5 meters in height. Average spread is 1 to 1.5 meters.

Hardiness: Trials to date show the variety hardy in USDA Zones 3 to 9.

Stems:

*Color.*—Young wood: Greyed-Orange 165A. Older wood: Greyed-Orange 166B.

*Internodes.*—Shape: Cylindrical. Length: 100 to 190 mm.

*Surface.*—Young wood: Smooth and pubescent. Older wood: Smooth and pubescent.

Plant foliage:

*Leaf characteristics.*—Deciduous.

*Mature leaf form.*—Trifoliate but often up to 5 to 7 leaflets arranged in pinnate form. Average leaflet count of 3.

*Compound leaf size.*—125 to 230 mm (l)×120 to 170 mm (w).

*Abundance.*—Above average.

*Color.*—Upper surfaces of mature leaves: Green Group 141A. Lower surfaces of mature leaves: Green Group 141C. Upper surfaces of new foliage: Yellow-Green Group 141C. Lower surfaces of new foliage: Yellow-Green Group 141D.

Plant leaves and leaflets:

*Stipules.*—Absent.

*Petioles.*—Average length: 75 to 100 mm. Color: Grey-Brown Group 199A. Clasping: By leaf petiole.

*Petioloule.*—Length: 5 to 15 mm. Color: Yellow-Green Group 144D.

*Leaflet shape.*—General shape: Elliptical. Base: Rounded. Apex: Acute. Margin: Entire.

*Leaflet size.*—20 to 25 mm in length by 10 to 15 mm wide.

*Leaflet texture.*—Upper side: Smooth. Lower side: Smooth. Pubescence: Not observed. Thickness: Moderate. Glossiness: Moderately Glossy Finish.

Disease resistance: Subject to any disease that normally attacks the species, however the variety is more tolerant to Botrytis, *Phoma clematadina*, and root diseases such as Theilaviopsis than some *Clematis*.

We claim:

1. A new and distinct variety of *Clematis* plant named 'Evipo032', described and illustrated herein, due to its abundant deep violet flowers, attractive long-lasting foliage and repeatable flowering under glasshouse conditions, suitability for production from softwood cuttings in pots, durable flowers and foliage which make the variety suitable for distribution in the floral industry.

* * * * *

Figure 2:
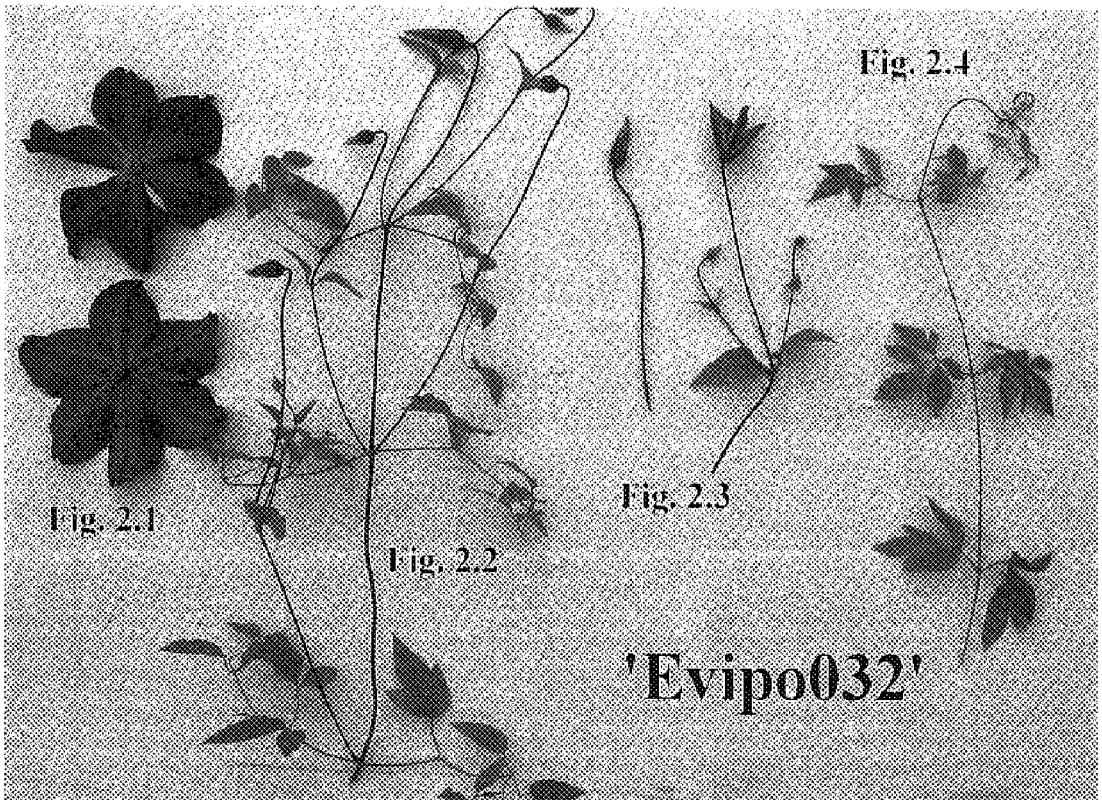
FIG. 2.1 Upper and lower surface of open flower.
Figure 3:
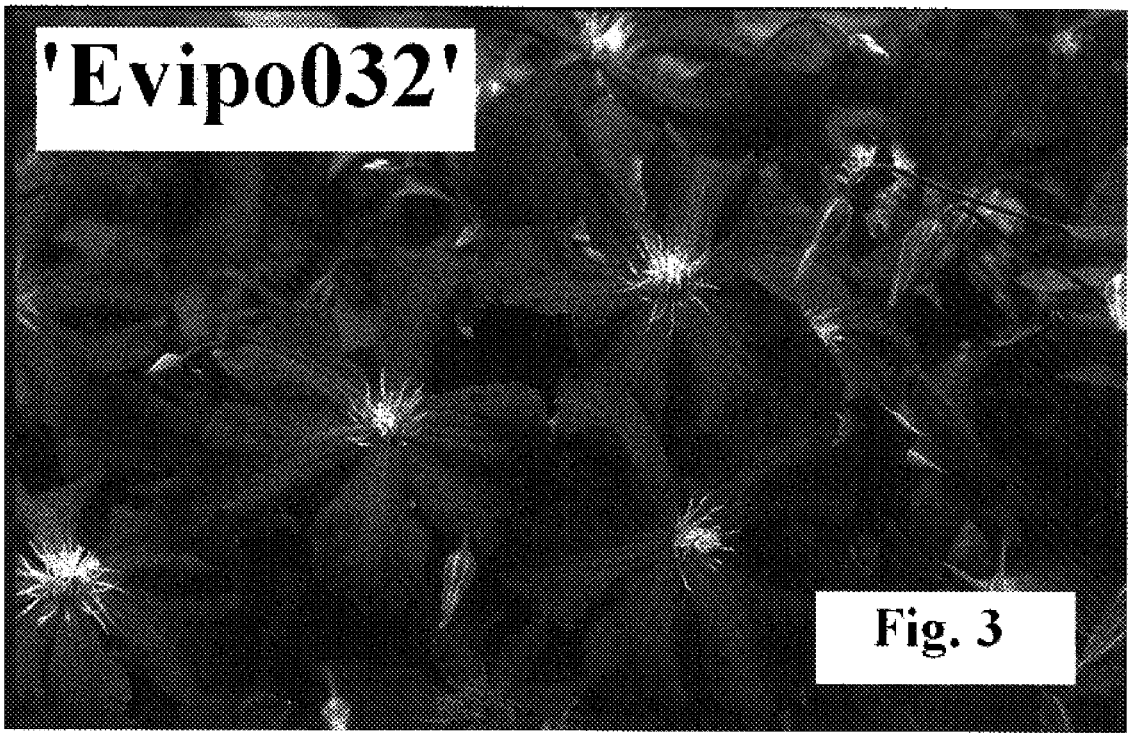
FIG. 3 Flower cluster showing open flowers and flower buds.

Fig. 2.4
Fig. 2.1
Fig. 2.2
Fig. 2.3
'Evipo032'